United States Patent
Tyler et al.

(10) Patent No.: US 6,456,866 B1
(45) Date of Patent: *Sep. 24, 2002

(54) FLAT INTERFACE NERVE ELECTRODE AND A METHOD FOR USE

(76) Inventors: Dustin Tyler, 38100 Tamarec Blvd., Apt. 204, Willoughby, OH (US) 44094; Dominique M. Durand, 36765 Valley Forge Dr., Solon, OH (US) 44139

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/409,315

(22) Filed: Sep. 28, 1999

(51) Int. Cl.[7] .............................. A61B 5/04; A61N 1/05
(52) U.S. Cl. ........................................ 600/377; 607/118
(58) Field of Search ........................... 600/377; 607/118

(56) References Cited

U.S. PATENT DOCUMENTS

| | | | |
|---|---|---|---|
| 3,654,933 A | * 4/1972 | Hagfors | ...................... 607/118 |
| 3,774,618 A | * 11/1973 | Avery | ......................... 607/118 |
| 4,573,481 A | 3/1986 | Bullara | |
| 4,602,624 A | 7/1986 | Naples et al. | |
| 4,920,979 A | 5/1990 | Bullara | |
| 5,092,332 A | * 3/1992 | Lee et al. | .................... 128/642 |
| 5,215,089 A | 6/1993 | Baker, Jr. | |
| 5,251,634 A | 10/1993 | Weinberg | |
| 5,282,468 A | 2/1994 | Klepinski | |
| 5,324,322 A | 6/1994 | Grill, Jr. et al. | |
| 5,344,438 A | 9/1994 | Testerman et al. | |
| 5,487,756 A | 1/1996 | Kallesoe et al. | |
| 5,505,201 A | 4/1996 | Grill, Jr. et al. | |
| 5,531,778 A | 7/1996 | Maschino et al. | |
| 5,634,462 A | * 6/1997 | Tyler et al. | .................. 128/642 |
| 5,824,027 A | 10/1998 | Hoffer et al. | |

OTHER PUBLICATIONS

Article in IEEE Transactions on Rehabilitation Engineering, vol. 5, No. 1, Mar. 1997; A Slowly Penetrating Interfascicular Nerve Electrode for Selective Activation of Peripheral Nerves; By Dustin J. Tyler and Dominique M. Durand, pp. 51–61.

(List continued on next page.)

Primary Examiner—Lee Cohen
(74) Attorney, Agent, or Firm—Ryan Krumholz & Manion

(57) ABSTRACT

A flat interface nerve electrode is provided along with a method for its use. The electrode provides a plurality of conductive elements embedded in a non-conductive cuff structure, which acts to gently and non-evasively redefine the geometry of a nerve through the application of a force so as to apply pressure to a nerve in a defined range, namely from 2 to 40 mmHG and more preferably from 15 to 30 mmHG and most preferably from 15 mmHG to 20 MMHG. This range is selected to minimize the reduction of blood flow within the tissue, which preferably is at least 70% of the initial value, more preferably 90% of the initial value. The cuff has an opening, which is elongated relative to the diameter of the nerve to which it is applied. Preferably, the cuff is constructed from an elastic bio-compatible material having top and bottom beam members configured to define a nerve opening. The cuff is open at one side and has a connection at the other side which results in a spring force being applied through the surfaces of the nerve opening to the subject nerve. During implantation the open sides of the cuff are closed so as to capture the nerve in the cuff. As the nerve is reshaped, specific nerve axons become more easily addressed through the epineurium by the embedded conductive elements.

17 Claims, 3 Drawing Sheets

OTHER PUBLICATIONS

Article in IEEE Transactions on Rehabilitation Engineering, vol. 5, No. 1, Mar. 1997; Recruitment Characteristics of Nerve Fascicles Stimulated by a Multigroove Electrode; By Paul Koole, Jan Holsheimer, Johannes J. Struijk, and Anton J. Verloop, pp. 40–50.

Article in Medical & Biological Engineering & Computing, May 1985; Neuromuscular stimulation selectively of mutliple–contact nerve cuff electrode arrays; by J.D. Sweeeney, N.R. Crawford, and T.A. Brandon; pp. 418–425.

Article from IEEE Transactions on Biomedical Engineering, vol. 35, No. 11, Nov., 1988; by Gregory G. Naples, J. Thomasf Mortimer, Avram Scheiner, James D. Sweeney; pp. 905–916.

Article from Electrodes for Peripheral Nerve Stimulation, Chap. 5; Overview of Peripheral Nerve Electrode Design and Implantation, by Gregory G. Naples, J. Thomas Mortimer and Ted G.H. Yuen; pp. 109–145.

* cited by examiner

FLAT INTERFACE NERVE ELECTRODE AND A METHOD FOR USE

FIELD OF INVENTION

The invention relates to implantable biomedical interfaces, and more particularly to a cuff for biological soft tissue which can be used as an electrode for selective stimulation and/or monitoring of nerve groups. Likewise, the cuff can be used as a delivery system for localized application of medication, such as bachlofin. The cuff also has application for use as a sensor for chemical removal.

BACKGROUND OF THE INVENTION

As the level of sophistication has increased in biomedical arts, advances have been made in implantable therapies. Therapies have evolved which involve the precise application of stimulus including electrical stimulus medication.

This invention relates in particular to a nerve electrode cuff for use in functional electrical stimulation. Functional electrical stimulation of the nervous system can be used to help to restore or maintain some degree of lost sensory and motor function in neurologically impaired individuals. In addition, there are certain specialized applications, such as the treatment of sleep apnea, where it is necessary to simultaneously monitor and generate electrical signals in nerves. The current invention extends to a method which both monitors and generates electrical signals in nerves, in particular of the hypo-glossal nerve for treatment of sleep apnea.

Prior art methods and apparatus which can be used in functional electrical stimulation and/or recording to restore a particular function broadly include:

(1) surface electrodes placed on the skin surface to activate nerves in a general region of interest;

(2) intra muscular and epimysial electrodes to activate nerves to individual muscles; and (3) the use of neural interfaces to address individual nerves.

Specific research in the area of nerve interfaces has involved nerve cuffs for stimulating and monitoring nerve activity. Cuff electrodes are used in peripheral nerve stimulation and produce function with up to 1000 times less charge than required by either surface or intra muscular electrodes. For example, peripheral nerve stimulation with a cuff requires less than 100 nC for full functional recruitment compared to up to 10 $\mu$C with surface stimulation or up to 4 $\mu$C for intramuscular electrical stimulation. The smaller power requirement may result in a potentially safer long term therapy. Other advantages of peripheral nerve electrodes include the fact that an entire muscle can be recruited from a single electrode. In addition, it may be easier to stimulate an appropriate peripheral nerve rather than some muscles which are difficult or impractical to implant with IM or epimysial electrodes (for example as in the larynx).

Prior art cuff electrodes have included proximity electrodes which are sutured into position. These electrodes require a relatively high amount of current. Half cuff electrodes are generally C-shaped, while cylindrical electrodes can be spiral, helical, split-cylinder, or chambered cylinders. C-shaped or split cylinder electrodes generally include a cylinder of dielectric material finding a bore having sufficient diameter to receive a nerve trunk to be electrically stimulated. Single or multiple annular electrodes can be positioned on the inner surface of the bore for applying electrical stimuli. The electrical stimuli, for example, may be used to provide functional electrical stimulation, to block neural nerve impulses traveling along the nerve trunk, or to cause other effects.

The spiral type of cuff electrode typically includes a self-curling sheet of non-conductive material biased-curl into a spiral. Conductive strips or pads are disposed on the self-curling sheet extending peripherally around the inner surface of the cuff. The conductive segments may be electrically conductive for applying electrical impulses or fluid conductive for infusing or extracting medications. In use, a first edge of a self-curling sheet may be disposed adjacent a nerve truck around which the cuff is positioned. The self-curling sheet is permitted to curl around the nerve forming an annular cuff. Helical electrodes wind around the nerve like a spring allowing nerve flex and fluid exchange with surrounding media (i.e. tissue).

Another approach to electrical stimulation of the nervous system involves small wire electrodes which penetrate the perineurium membrane and are advanced into a fascicle of the nerve, within fascicular endoneurium. This method has the disadvantage of being highly invasive and can result in permanent damage to the nerve through penetration of the perineurium and mechanical trauma to the axons.

Regeneration type neural interfaces are comprised of a thin silicon diaphragm with many small holes, which is positioned between the cut ends of a peripheral nerve. Over time the axons will regenerate through the many small holes in the diaphragm. A disadvantage to this therapy is that it requires the nerve to be severed. As well, axons tend to regenerate around the interface rather than through it.

SUMMARY OF INVENTION

The present invention contemplates a soft tissue cuff for use for example, as a nerve cuff electrode. The invention has application in addition for medicinal infusers and implantable biomedical devices for introducing, monitoring, or removing matter, fluids or energy. In contrast to prior art cuffs, the present invention is intended to apply a small, non-circumferiential force over time; this results in a non-damaging pressure within the intrafascicular endonurium so as to effect the nerve shape but not as to occlude blood flow within the nerve. The cuffs of the present invention may be implanted without damage to the subject nerve. Further, the cuff can allow for tissue swelling and movement. The present invention causes the nerve to mimic its natural reaction to forces applied within the body. Specifically, the body naturally applies small forces to the nerves which results in flattening or other shape changes to the nerve. An example of these forces is illustrated by the flattening of the sciatic nerve as it exits the pelvis at the sciatic foramen. Further, some nerves will take on an ellipsoidal shape as they pass through muscle planes. Other nerves have demonstrated significant flattening over time as a result of tumor pressure.

In a preferred embodiment, the present invention recognizes a small range of pressure which will cause nerve reshaping without damaging the nerve. In particular, this cuff electrode is designed to apply a force that does not cause pressure to rise above 40 mmHG (or more specifically, does not cause a reduction of blood flow to less than 70% of normal (i.e., baseline)). It is currently believed that tissue pressure correlates with blood flow. Specifically, at less than 10 to 15 mmHG, there is little effect on blood flow. At the range of 15 to 20 mmHG the venus blood flow is initially impaired. At 30 mmHG the capillary and arterial blood flow is first impaired. By 80 mmHG, neural blood flow stops completely. In compressive pathologies, such as carpal tunnel syndrome, damage and pain do not occur until the neural pressure is greater than 30 mmHG. Consequently, the current invention is intended to apply a force resulting in an internal nerve pressure of between about 5 mmHG and 40 mmHG, and more preferably between 15 mmHG and 30 mmHG, and even more preferably from 15 mmHG to 20 mmHG.

The current invention has the object of solving the deficiencies in the prior art. The present invention has the advantage of providing selectively, i.e. the ability to activate and record a specific population or subset of axons within a nerve.

A soft tissue cuff is provided which is non-invasive to the soft tissue. Further, the electrode is more compact in at least one dimension and may lower charge requirements as it allows for more selective stimulate on specific axons, and especially the central axons. Since the perineurium is reshaped over time, damage to this protective neural tissue is minimized.

In accordance with the present invention a nerve cuff is provided which applies the defined pressure to a nerve to cause gradual reshaping over time. This pressure is applied in a way to allow the nerve to adapt to the condition without damage to the nerve. Of course, it should be understood that the amount of time will vary with the nerve as some nerves may adapt faster than others. The required time for reshaping may be 24 hours or as little as 2 hours or up to 1 week or more. The quality and condition of the nerve will also contribute to this time for reshaping.

In a first embodiment, the invention includes an elongated, substantially rectangular central opening having a height, which is smaller than and a width which is longer than the diameter of the nerve to which it is applied. The cuff may be made of a material having a sufficient elasticity and a shape sufficient to cause a force applied selectively across the transverse direction of the nerve. The nerve cuff can be open at a single end or alternatively the nerve cuff may be open at two ends. The open ends are closed such as by staple, an O-ring in a grooved area, a suture, a mechanical interference fit or other closure mechanism. The beams which form the top and/or bottom of the nerve cuff and the connecting juncture for these beams have a structure and/or material characteristic tailored to impart a particular pressure to the nerve.

In a further embodiment, the invention can be used both to record sensory neural activity and stimulate motor output. This capability from a single device would be very beneficial for closed loop systems in applications such as restoring hand grasp or obstructive sleep apnea.

DETAILED DESCRIPTION

Figure 1:
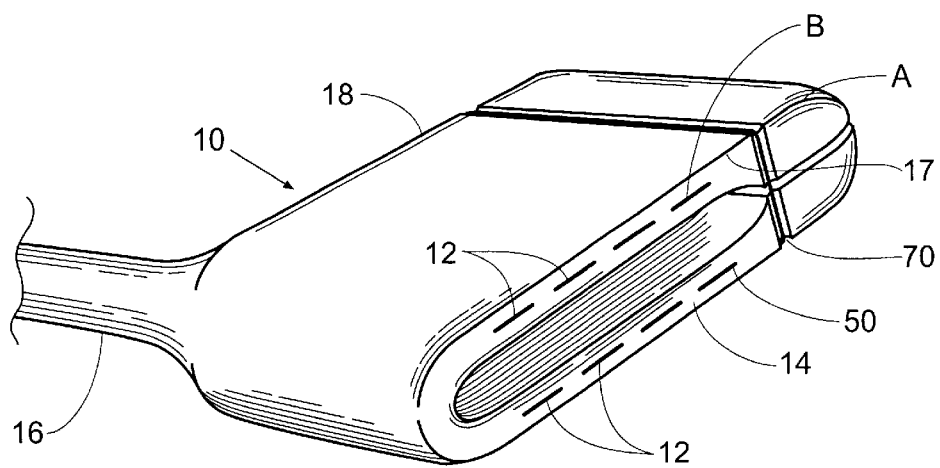
FIG. 1 is a perspective view of a first embodiment of the nerve cuff in accordance with the invention.

A nerve cuff in accordance with the invention as illustrated generally at 10 the cuff includes a non-conductive band 14 and segments B which are electrically conductive electrodes 12. while this specification describes the cuff in association with a nerve, it is to be understood that the cuff is also adapted for use with other soft tissue, such as muscle.

The band 14 encircles the nerve and gently and non-invasively applies a defined exterior force over time to redefine the geometry of the nerve, such as by flattening. Through simple modification of the structure of the electrodes 12, such as by forming fluid conduits or ducts, the elements are adaptable to become medication or fluid conductive. In addition, a selected one or more of the conductive segments may be adapted to be medication conductive while the other segments are adapted to remain electrically conductive for a combined chemical and electrical stimulation. Further, chemical and electrical conduction is not constrained to flow only into the nerve from the cuff. Rather, as a significant aspect of the invention, the chemical and electrical conductive elements may also be adapted to conduct chemicals and electricity both from the cuff to the nerve and into the cuff from the nerve for stimulating and monitoring various nerve properties, activities, and characteristics, respectively. Accordingly, the cuff is also useful in such applications as treatment of sleep apnea where combined sensor/effector cuff electrodes may be beneficial, for example, for use in monitoring activity on the hypoglossal nerve. U.S. Pat. No. 4,830,008 to Meer, incorporated herein by reference, describes a preferred method and generic apparatus for treating sleep apnea. The present invention extends the preferred cuff embodiments to the Meer teachings for use in treating sleep apnea.

With further continued reference to FIGS. 1–7, each of the plurality of electrodes 12 are individually connected through a single lead 16 to an operatively associated electrical signal generating source (not shown) or electrical monitoring device (not shown). In the FIGS., the fine conductive wires are illustrated as a plurality of individual conductors 50 which extend longitudinally from the conductive segments B to a location between the first edge 17 and the second edge 18 of the implantable cuff. From that point, the plurality of conductors extend through implantable cuff to a common exit area within a lead 16. There, the plurality of conductors 50 extend away from the nerve encircled by the implantable cuff for subsequent attachment to the operatively associated electrical signal or monitoring devices(s). In the preferred embodiment, the plurality of conductors 50 extend from the conductive segments B completely embedded in the non-conductive material comprising the cuff sheet A. In this way, they are insulated from direct contact with either the nerve, other conductors, or other surrounding tissue. Also, the non-conductive sheet A acts as a reinforcing structure and affords a level of structural integrity to the somewhat otherwise frail conductors.

Although the preferred embodiment includes electrically conductive segments B having one or more discrete electrodes disposed thereat, one alternative includes forming a micro-multielectrode array in silicon using semiconductor fabrication technology. An example of this approach is set forth in U.S. Pat. No. 5,324,322 to Grill Jr., et al., and in Wim L. C. Rutten, Harmen J. Van Wier and Johan H. M. Put, "*Sensitivity and Selectivity of Intraneural Stimulation Using a Silicon Electrode Array,*" *IEEE Trans. Biomed., Eng.* Vol. 38, pp. 192–198, February 1991. J. F. Hetke, J. L. Lund, K. Najafi, K. D. Wise, and D. J. Anderson "*Silicon Ribbon Cables for Chronically Implantable Microelectrode Arrays*", *IEEE Trans. Biomed., Eng.* Vol. 41, pp. 314–321, April, 1994. Using this and similar technologies currently available including micro-lithography and micro-integrated electronics, the plurality of conductors may be formed on fine flexible silicon substrates, or polyimide or metalized polymer. In this way, active and intelligent electronics may be included on the cuff apparatus itself.

Figure 2:
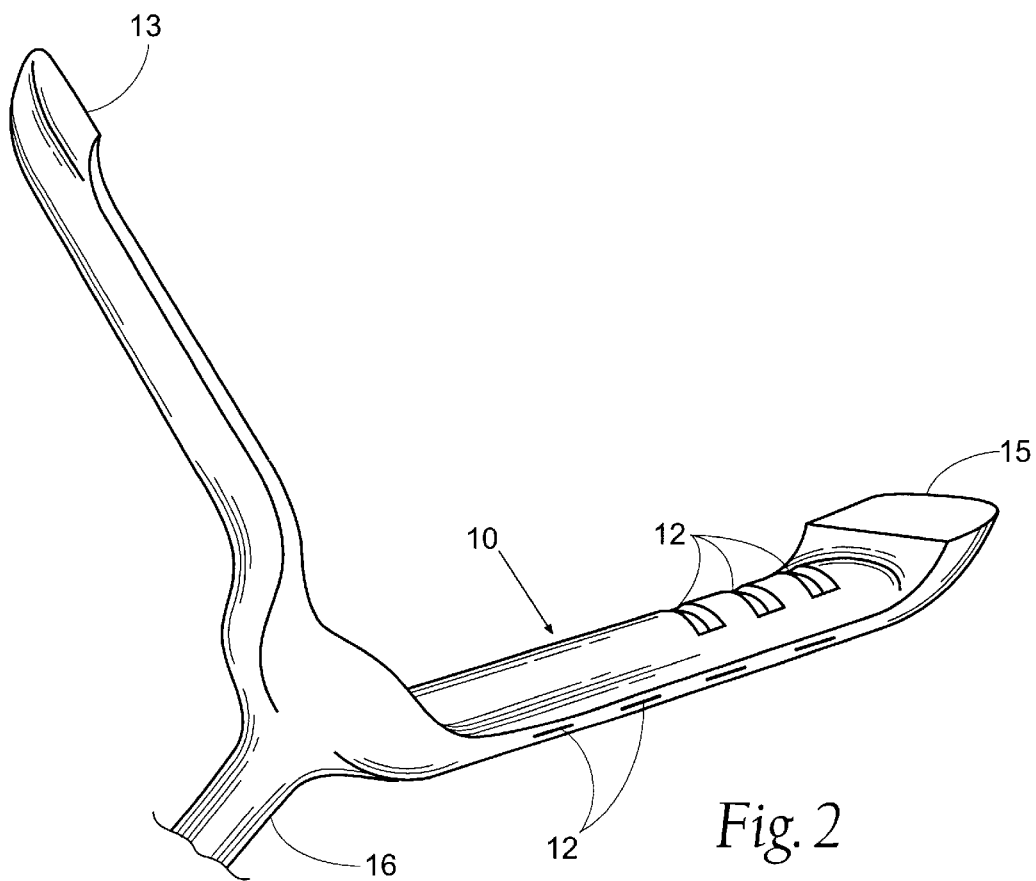
FIG. 2 is a view of the nerve cuff electrode when it is opened.

In use, the subject nerve 60 is surgically accessed and the open side of the cuff is slipped over the nerve in the desired position. The cuff is opened as is shown in FIG. 2 to completely encircle the nerve at which point the two open and opposing ends 13, 15 are connected together. Preferably, a connector arrangement such as an o-ring, staple or suture 70 is used to join the ends 13, 15.

Figure 3:
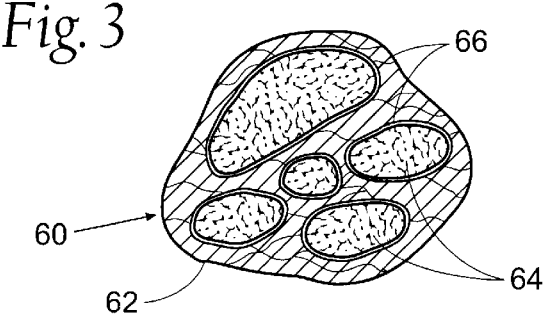
FIG. 3 is a view of the nerve in an initial state.
Figure 4:
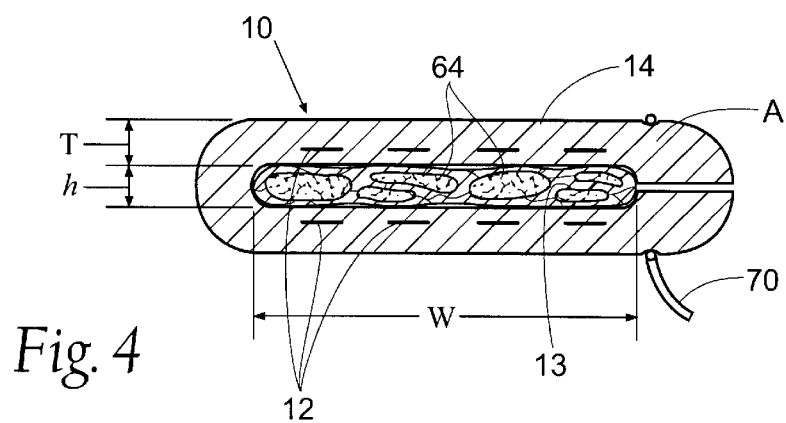
FIG. 4 is a view of the nerve cuff on a nerve after (reshaping has occurred.
Figure 5:
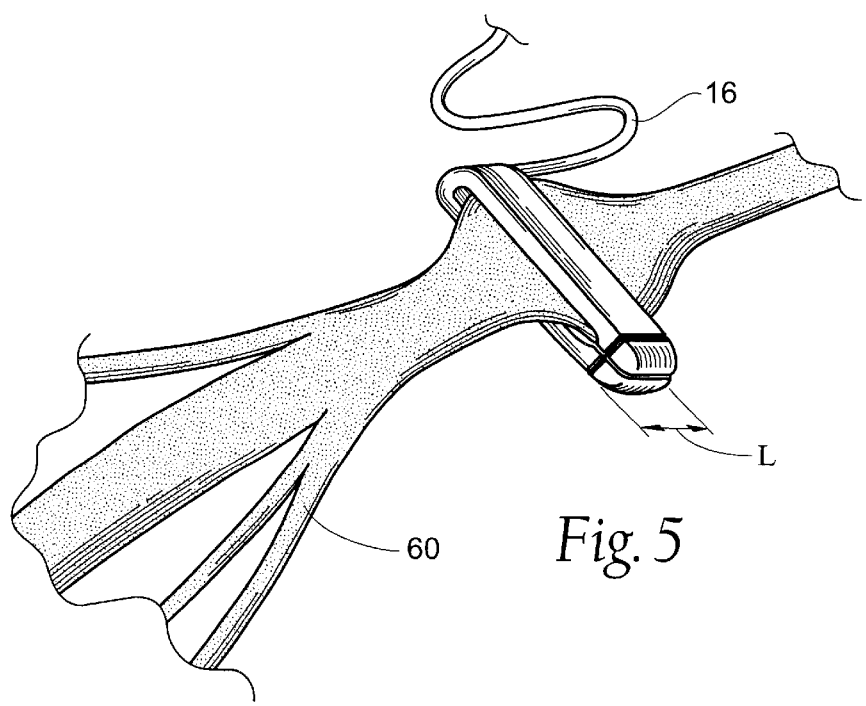
FIG. 5 is a perspective view of the nerve cuff on a nerve.

FIGS. 4 and 5 illustrates the flat interface nerve cuff electrode of the first preferred embodiment on a nerve 60 on a nerve which has responded to the application of pressure by the cuff to reshape into a final flattened state. FIG. 3 illustrates a nerve in its initial state.

In general, the nerve 60 is surrounded by a loose membrane called the epineurium membrane 62. The nerve is typically organized into several groups of axons called fascicles 64. Each fascicle 64 is surrounded by a membrane called the perineurium membrane 66. In this embodiment, the flat interface nerve cuff slowly applies transverse pressure to opposing surfaces of the nerve, so as to spread the fascicles 64 and flatten the epineurium membrane 62 (and even ultimately of the perineurium with a corresponding reshaping of the fascicles themselves) of the target nerve 60. This flattening action effectively allows the conductive members B on the sheet A to contact particular fascicle through the epineurium membrane 62 without puncturing either the perineurium membrane 66, or the epineurium. Instead, the fascicles 64 are displaced with a subsequent reshaping of the epineurium membrane 62 at locations corresponding to the cuff interface. The method of using this and the other preferred embodiments contacts electrodes with specific nerve fascicles without penetration of the perineurium membrane. Typically, the time period required for the cuff to function properly extends from about one (1) hour to several days depending upon particular application and situation.

The driving force, which motivates the conductive members B inward, however, is provided by the mechanical spring action at the active end of the cuff as well as by the elastic nature of the cuff material. This unique design illustrated in the figures allows the superficial placement of the electrodes with selective access to the entire axon population but with minimal damage to the nerve itself. The electrodes 12 are each capable of activating separate and distinct regions with the nerve, along both the longitudinal and radial axis of the nerve, which was not previously accessible by other types of electrodes without the associated damage described in the background above. The electrodes are also capable of sensing small neural signals with better signal to noise rations due to the close proximity of each of the electrodes to the axons comprising the fascicles.

The lower limit of applied pressure required to reshape the nerve is something greater than that which is naturally occurring in an occurring nerve. This pressure is usually in the vicinity of 2 mmHG.

It is to be appreciated that by controlling the spring constant or force exerted by the cuff surfaces, the cuff can be configured to rest against the surfaces of the epineurium membrane. FIG. 4 illustrates the cuff in this type of situation, with contact points depicting a portion of the cuff resting on the surface. The desired pressure, which results from the force applied by the cuff is from about 2 to about 80 mmHG; preferably from about 3 to about 30 mmHG and most preferably from about 5 to about 15 mmHG. This pressure is measured as is dis-cussed in the following examples. It is to be further understood that such surface implementation may be accomplished by all the remaining embodiments as well.

Figure 6:
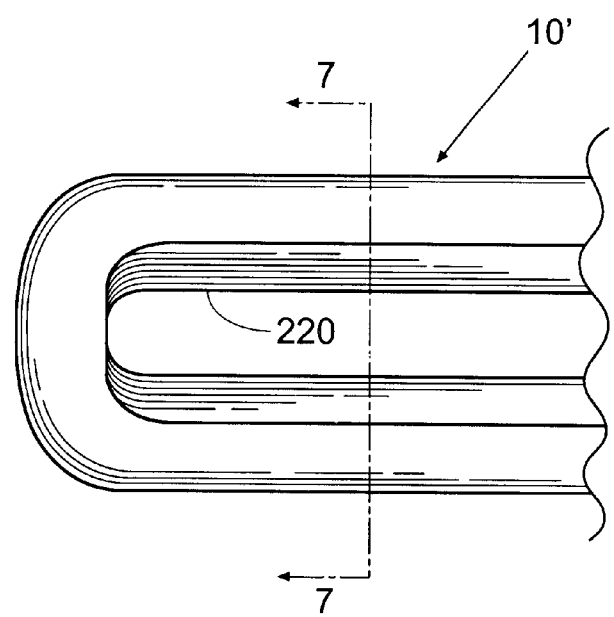
FIG. 6 is a detail of a side view of a second embodiment.
Figure 7:
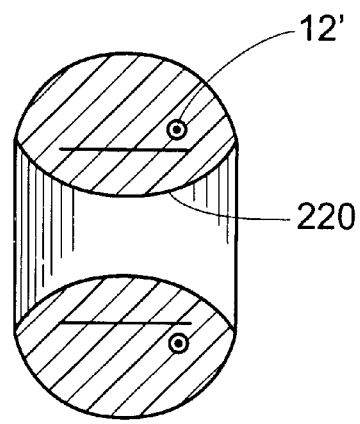
FIG. 7 is an end cross-section of the embodiment of FIG. 6.

The embodiment shown in FIGS. 6 and 7 varies from the first embodiment as it has a radiused surface 220 for the nerve interface. The gradual curve resulting from the radial surface provides an imposed transition zone to minimize strain on the tissue.

The present invention involves a flat interface nerve electrode (FINE) shown in FIG. 1 that applies small forces on opposing sides of the nerve while allowing the nerve to expand in other directions. The hypothesis is that a small force does not significantly decrease nerve blood flow and will reshape the nerve into an elongated or flattened oval geometry that approximates the "ideal" geometry of a flat cable.

The FINE is shown as a pair of beams closed at the ends to form a rectangular opening. Electrical contacts are embedded in the walls. When the electrode is first placed around a nerve, the beams are deformed around the nerve. The thickness (t), width (w), length (l), and cross-sectional profile of the beams of the electrode will determine the magnitude of the force that will be applied to the nerve.

Compared to a circular geometry, the flat geometry of the present invention offers several advantages. For the same cross-sectional area, the circumference of the flattened geometry is larger, allowing more contacts to be placed around the nerve. The maximum distance from any axon to an electrical contact on the FINE is smaller than for a circular electrode, effectively moving central tissue to the surface of the nerve. The flat geometry aligns the nerve fascicles to increase selectivity and access to every fascicle.

The feasibility of reshaping electrodes requires that the force that reshapes the nerve is less than the force that causes axon damage or loss. The following examples summarize studies of the FINE selectivity and chronic safety.

EXAMPLE I

In acute experiments the FINE was implanted on the sciatic nerve of six cats for 36 hours and tested for reshaping and selective stimulation. The nerve geometry was measured from histology of the nerve cross-section. The FINE aligned and significantly ($p<0.0001$, Wilcoxon Rank-sum test of eccentricity measurements) reshaped the fascicles compared to the proximal or distal sections of the nerve.

Monopolar stimulation from contacts on the FINE selectively reproduced the individual outputs of the major fascicles of the common sciatic nerve in 12 of 14 trials (86%). The FINE, therefore, demonstrated the ability to selectively activate sub-populations of axons within the common sciatic nerve.

EXAMPLE II

FINE electrodes were also implanted chronically on the sciatic nerve of 40 rats. FINEs of three different wall thickness, t in FIG. 4, (FIG. 2), were implanted for 1, 7, and 28 days and compared to sham implants. The thicker the wall thickness, the greater the force applied to the nerve. Nerve physiology was assessed weekly by measurements of the footprint during normal gait. Only the FINE with the greatest wall thickness produced any changes in the nerve physiology. The changes were significantly different ($p<0.05$, two-tail t-test of the mean) from the sham trials only between 1 and 14 days post-implant and had recovered by 21 days post-implant. Measurement of nerve geometry demonstrated that all three FINE designs significantly reshaped the nerve and fascicles compared to sham (p<0.05, Wilcoxon Rank-sum test of eccentricity measurements).

The histology of sham trials was not different than the histology from nerves implanted with the smallest wall thickness FINE. The FINE with the thickest wall produced changes in the nerve histology that indicated a remyelination process and demonstrated evidence of axon sprouting and regeneration. The intermediate thickness FINE demonstrated mixed results and appeared to be sensitive to surgical manipulation. The blood-nerve-barrier permeability was examined using fluoroscopic techniques (Rydevik and Lundborg 1977; Lundborg 1983). The thin walled FINE results were not significantly different from the sham results, the intermediate thickness FINE gave mixed results, and the thick walled FINE significantly increased the blood-nerve barrier permeability.

Acute stimulation experiments with a preliminary FINE show that an electrode that produces a flattened nerve geometry can selectively stimulate different unique functions within a common nerve trunk. Chronic trials have shown that a thin walled FINE, which applies small forces to the nerve, can reshape the nerve without damage. The preliminary FINEs were designed by trial and error testing on the specific nerve to be implanted. This is not adequate for commercial electrode development, which requires a systematic design approach and rigorous safety guidelines.

While in accordance with the patent statutes the best mode and preferred embodiment has been set forth, the scope of the invention is not limited thereto, but rather by the scope of the attached Claims.

What is claimed is:

1. A system for functional electrical stimulation and recording comprising
    a cuff for a nerve or muscle filament, the filament having an external configuration with a height Y and a width X, the cuff comprising an elastic collar member defining an internal opening which has an internal configuration having a height less than Y and a width greater than X, said collar member including a material that exerts a force on said filament which will cause the filament to gradually reshape to the internal configuration of said opening and wherein the resulting pressure in said filament is less than 80 mmHG, and
    an electrode interface carried by the elastic collar member including a plurality of electrodes spaced side by side for contact along a surface of the filament;
    an array of conductors coupled to the electrodes;
    a stimulation apparatus coupled to at least one of the conductors and that can be operated to stimulate the filament; and
    a property monitoring apparatus coupled to at least one of the conductors and that can be operated to monitor a biological property of the filament.

2. A system as set forth in claim 1, wherein said collar member has a top beam and a bottom beam.

3. A system as set forth in claim 2, wherein said top beam has a first side joined to a first side of said bottom beam by a web member.

4. A system as set forth in claim 1, wherein said collar member comprises an elastomeric material.

5. A system as set forth in claim 4, wherein said collar member comprises a silicon elastomer.

6. A system as set forth in claim 1, wherein said collar member exerts a force which results in a pressure in said filament of from about 2 to about 50 mmHG.

7. A system as in claim 1
    wherein the nerve or muscle filament has a blood flow Z, and
    wherein the blood flow in the nerve or muscle filament is not reduced to less than 70% Z.

8. A system as set forth in claim 7, wherein said internal opening has a radiused area so as to define a gradual tapering toward the center of said internal opening.

9. A system as set forth in claim 8, wherein said blood flow is not reduced to less than 85% of Z.

10. A method of functional electrical stimulation and recording comprising the steps of;
    providing a stimulation apparatus, which, when operated, stimulates a nerve or muscle filament;
    providing a monitoring apparatus, which, when operated, monitors a biological property of a nerve or muscle filament;
    placing a cuff around a nerve or muscle filament, the nerve or muscle filament having a height Y and a width X the cuff comprising
        an elastic collar member defining an internal opening which has an internal configuration having a height less than Y and a width longer than X, the collar member including a material that exerts a force on the nerve or muscle filament which will cause the nerve or muscle filament to gradually reshape to the internal configuration of the opening and wherein the resulting pressure in the nerve or muscle filament is less than 80 mmHG, and
        an electrode interface carried by the elastic collar member including a plurality of electrodes spaced side by side for contact along a surface of the nerve or muscle filament;
    an array of conductors coupled to the electrodes;
    coupling at least one of the conductors to the stimulation apparatus;
    coupling at least one of the conductors to the monitoring apparatus;
    applying a gradual force to the nerve or muscle filament by means of the cuff which results in a pressure in the nerve or muscle filament of less than 80 mmHg;
    operating the stimulation apparatus and;
    operating the monitoring apparatus.

11. A method as forth in claim 10, wherein said cuff comprises an elastic material.

12. A method as set forth in claim 11, wherein said elastic material is a silicon elastomer.

13. A method as set forth in claim 10, wherein said nerve filament is part of the hypo-glossal nerve.

14. A method as in claim 10
    wherein the nerve or muscle filament has a blood flow Z, and
    wherein the blood flow in the nerve or muscle filament is not reduced to less than 70% Z.

15. A method as set forth in claim 14, wherein said nerve filament is part of the hypo-glossal nerve.

16. A method as in claim 10
    wherein the stimulation apparatus and the monitoring apparatus are operated simultaneously.

17. A method as set forth in claim 16, wherein said simultaneous operating of the monitoring and stimulating apparatus is intermittent with no operation of the monitoring or stimulation apparatus, or with operating only the monitoring apparatus or only the stimulating apparatus.

* * * * *